(12) United States Patent
Castiel et al.

(10) Patent No.: US 8,951,775 B2
(45) Date of Patent: Feb. 10, 2015

(54) COSMETIC USE OF MICROORGANISMS FOR THE TREATMENT OF OILY SKIN

(75) Inventors: Isabelle Castiel, Nice (FR); Audrey Gueniche, Rueil Malmaison (FR)

(73) Assignees: L'Oreal, Paris (FR); Nestec SA, Vevey (CH)

(*) Notice: Subject to any disclaimer, the term of this patent is extended or adjusted under 35 U.S.C. 154(b) by 293 days.

(21) Appl. No.: 13/056,344

(22) PCT Filed: Jul. 23, 2009

(86) PCT No.: PCT/IB2009/053204
§ 371 (c)(1),
(2), (4) Date: Apr. 15, 2011

(87) PCT Pub. No.: WO2010/013179
PCT Pub. Date: Feb. 4, 2010

(65) Prior Publication Data
US 2011/0182861 A1    Jul. 28, 2011

(30) Foreign Application Priority Data
Nov. 19, 2008 (FR) ..................... 08 57866

(51) Int. Cl.
*A61K 35/74* (2006.01)
*A61Q 19/00* (2006.01)
*A61K 8/99* (2006.01)

(52) U.S. Cl.
CPC ............. *A61Q 19/008* (2013.01); *A61K 8/99* (2013.01); *A61Q 19/00* (2013.01); *Y10S 514/859* (2013.01); *Y10S 514/864* (2013.01)
USPC ......................... 435/252.9; 514/859; 514/864

(58) Field of Classification Search
None
See application file for complete search history.

(56) References Cited

U.S. PATENT DOCUMENTS

| | | |
|---|---|---|
| 2003/0049231 A1 | 3/2003 | Baur et al. |
| 2006/0002910 A1 | 1/2006 | Baur et al. |
| 2006/0008453 A1* | 1/2006 | Breton et al. ............. 424/93.45 |
| 2006/0171936 A1* | 8/2006 | Gueniche et al. .......... 424/93.45 |
| 2006/0269508 A1* | 11/2006 | Trejo ............................ 424/74 |
| 2009/0232785 A1 | 9/2009 | Breton et al. |
| 2010/0272839 A1 | 10/2010 | Gueniche et al. |
| 2010/0278793 A1 | 11/2010 | Gueniche et al. |
| 2011/0014248 A1 | 1/2011 | Castiel et al. |

FOREIGN PATENT DOCUMENTS

| | | |
|---|---|---|
| EP | 1 110 555 | 6/2001 |
| EP | 1 609 463 | 12/2005 |
| FR | 2 872 047 | 12/2005 |
| FR | 2 889 057 | 2/2007 |
| WO | 01 13927 | 3/2001 |
| WO | 02 28402 | 4/2002 |
| WO | 03/068250 | 8/2003 |
| WO | 03 070260 | 8/2003 |
| WO | 2005/091933 | 10/2005 |
| WO | 2006 037922 | 4/2006 |

OTHER PUBLICATIONS

International Search Report issued Nov. 17, 2009 in PCT/IB09/053204 filed on Jul. 23, 2009.
Office Action as received in the corresponding Japanese Patent Application No. 2011-520636 dated Nov. 8, 2013 w/English Translation.

* cited by examiner

*Primary Examiner* — Allison Fox
*Assistant Examiner* — Yvonne Pyla
(74) *Attorney, Agent, or Firm* — Oblon, Spivak, McClelland, Maier & Neustadt, L.L.P.

(57) ABSTRACT

The present invention relates to the cosmetic use of an effective amount of at least one probiotic microorganism and/or a fraction thereof and/or a metabolite thereof, as an agent for treating and/or preventing oily skin or skin with an oily tendency and the associated skin disorders.

10 Claims, No Drawings

COSMETIC USE OF MICROORGANISMS FOR THE TREATMENT OF OILY SKIN

The present invention relates to the field of cosmetic and/or dermatological products, more particularly for use in the care of oily skin.

In particular, the present invention aims to propose the use of a new active agent for treating and/or preventing disorders associated with oily skin, in particular through an action where sebum secretion is reduced.

Sebum normally constitutes a hydrating agent for the epidermis.

It is the natural product of the sebaceous gland which constitutes an annexe of the pilosebaceous unit. It is essentially a more or less complex mixture of lipids. Conventionally, the sebaceous gland produces squalene, triglycerides, aliphatic waxes, cholesterol waxes and, possibly free cholesterol (Stewart, M. E., *Semin Dermatol* 11, 100-105 (1992)). The action of bacterial lipases converts a varying part of the triglycerides formed so as to give free fatty acids.

The sebocyte constitutes the competent cell of the sebaceous gland. Sebum production is associated with a programme of terminal differentiation of this cell. During this differentiation, the metabolic activity of the sebocyte is essentially focused on lipid biosynthesis (lipogenesis) and more specifically on fatty acid neosynthesis.

Hyperseborrhoeic oily skin is characterized by exaggerated secretion and excretion of sebum. Conventionally, a sebum level of greater than 200 µg/cm$^2$ measured on the forehead is considered to be characteristic of such oily skin.

Such skin is also often associated with a desquamation defect, a glistening complexion and a thick skin grain, manifestations which are felt to be skin imperfections or aesthetic disorders.

In addition to its unsightly appearance, it constitutes a territory on which complications can occur. It affects the areas where there are many sebaceous glands and results mainly from an androgenic overstimulation of sebaceous production by these specific glands. Thus, hyperseborrhoea contributes to the occurrence of acne vulgaris lesions.

Acne is a multifactor disease which affects skin rich in sebaceous glands (face, shoulder area, arms and intertrigenal areas). It is the most common form of dermatosis.

In its mildest form, this dermatosis affects almost each human being. Its frequency is at a maximum during puberty, but it can manifest itself for the first time from 7 to 9 years of age and up to ages exceeding 40. It moreover affects both men and women.

Among its most common forms, mention may be made of comedonal acne, commonly known as juvenile acne, papulopustular and/or nodular acne, acne conglobata and "exogenous" acne which appears as a reaction to inflammatory external factors.

More specifically, acne is a disease of the sebaceous gland follicle. The following five pathogenic factors play a determining role in the formation of acne:
  genetic predisposition,
  overproduction of sebum (seborrhoea),
  androgens,
  follicular keratinization disorders (comedogenesis), and
  bacterial colonization and inflammatory factors.

In fact, in the deepest parts of the infundibular portion of the hair follicle, the formation of a greater than normal amount of keratinocytes is observed. These cells differentiate to give horny cells which gradually obstruct the lumen of the follicular canal. The physiological process of continuous desquamation of the acro-infundibulum towards the surface is disturbed by the increased adhesion of the horny cells produced. A hyperkeratotic plug forms, constituting the comedone, the initial lesion of acne. Finally, the three predominant local microorganisms, *Staphyloccus epidermidis*, *Malassezia furfur* and *Propionibacterium acnes* find an ideal nutritive environment in the sebaceous follicle. The alteration of the environment and the improvement in the growth conditions for the microflora lead to an increase in pro-inflammatory products such as lipases, proteases and interleukins. It is accepted that the lipases produced dissociate the triglycerides to give free fatty acids which, acting as irritants for the follicular epithelium, subsequently stimulate hyperproliferation. Granulocytes are attracted, thereby intensifying the inflammatory process, and said granulocytes migrate into the lumen of the follicle, where they finally contribute to the enzymatic rupture of the follicle wall.

The clinical manifestations, known as retentional manifestations, observed may be of open or closed comedone type (microcyst, microcomedone, whitehead). The inflammatory lesions derived from the retentional lesions may be of papule or pustule type, with hardened nodules, abscesses, fistulae, scarring.

Thus, acneic and acne-prone individuals most commonly have oily skin, skin with an oily tendency or combination skin. Their skin is most commonly shiny, with numerous imperfections inter alia of the face (microcysts, microcomedones, whiteheads, papules, pustules, with hardened nodules, abscesses, fistulae, scarring). The imperfections may also be of the type such as dull, muddy skin, dyschromia, redness, or rough skin with patches of dry skin. Cutaneous hyperkeratosis is observed, on the face the pores are dilated, with the skin often being rough with a thick stratum corneum, giving the appearance of areas of dry skin in patches (epidermal atrophy and slight desquamation).

Consequently, hyperseborrhoea is clearly a biological phenomenon that it appears to be important to control effectively in order to prevent the manifestation of associated skin disorders.

In order to combat hyperseborrhoea, various compounds which, when applied topically to the skin, are capable of reducing lipogenesis in the sebocytes and consequently limiting sebum production, have been proposed.

Unfortunately, the treatments currently available are not entirely satisfactory, in particular in terms of the side effects which are frequently associated therewith, such as irritant side effects with certain topical agents such as retinoids and benzoyl peroxides, or even gastrointestinal side effects (oral antibiotic treatment). In addition, resistance of *P. acnes* to certain local antibacterial treatments is frequently observed.

There therefore remains a need to have new active agents capable of exerting a beneficial cosmetic or therapeutic action on oily skin or skin with an oily tendency.

There also remains a need to have active agents that make it possible to re-establish the eco flora of oily skin.

There also exists a need to have new compositions that are effective for treating and/or preventing oily skin or skin with an oily tendency and that are pleasant and comfortable to use, thus promoting compliance with the treatment.

There also exists a need to have new active agents which make it possible to treat and/or prevent oily skin disorders, especially such as seborrhoeic dermatitis and, in particular, acne.

The object of the present invention is to meet these needs.

Thus, according to a first subject, the invention relates to the cosmetic use of an effective amount of at least one probiotic microorganism, especially of the *Lactobacillus* sp. and/or *Bifidobacterium* sp. genus, of a fraction thereof and/or a metabolite thereof, as an active agent for treating and/or preventing oily skin or skin with an oily tendency and the associated disorders.

The inventors have noted, in fact, that such a microorganism is found to be effective for the treatment and/or prevention of disorders associated with oily skin and/or skin with an oily tendency.

For the purpose of the present invention, the term "skin" is intended to mean the skin of the face or of the body.

For the purpose of the present invention the term "effective amount", is intended to mean an amount sufficient to obtain the expected effect.

For the purpose of the present invention the term "prevent" is intended to mean the fact of reducing the risk of occurrence of the manifestation of the disorder under consideration.

To the inventors' knowledge, this effectiveness of a probiotic microorganism, especially of the *Lactobacillus* sp. and/or *Bifidobacterium* sp. genus, of a fraction thereof and/or of a metabolite thereof, has never been described.

The use of microorganisms, in particular probiotic microorganisms, for skin care has already been described.

Thus, document WO 2006/07922 describes compositions dedicated to the treatment of sensitive skin, using, as active agent, a combination of a *Lactobacillus paracasei* or *casei* microorganism and of a *Bifidobacterium longum* or *Bifidobacterium lactis* microorganism.

FR 2 872 047 describes, for its part, a combination of a probiotic microorganism with a divalent inorganic cation.

As for FR 2 889 057, it discloses a topical composition comprising a probiotic microorganism in combination with a polyunsaturated fatty acid and/or polyunsaturated fatty acid ester, that is of use in the treatment of sensitive skin.

In addition, WO 02/28402 describes the use of probiotic microorganisms for regulating hypersensitivity reactions of the skin, such as inflammatory and allergic reactions.

Finally, WO 03/070260 relates to the use of probiotic microorganisms for the purposes of photoprotection of the skin.

Consequently, none of these documents describes the use of probiotic microorganisms according to the invention, especially of the *Lactobacillus* and/or *Bifidobacterium* sp. genus, and in particular of the *Lactobacillus paracasei* ST11 strain, a fraction thereof and/or a metabolite thereof, as an active agent that is of use in the treatment and/or prevention of oily skin or skin with an oily tendency and associated skin disorders.

A subject of the invention is also the cosmetic, preferably topical, use of an effective amount of at least one probiotic microorganism according to the invention, especially of the *Lactobacillus* and/or *Bifidobacterium* sp. genus and in particular of the *Lactobacillus paracasei* ST11 strain, a fraction thereof and/or a metabolite thereof, as an active agent for treating and/or preventing seborrhoeic dermatosis associated with oily skin or skin with an oily tendency.

The present invention is also directed towards the cosmetic use of the abovementioned microorganism, as an active agent for treating and/or preventing the lesions and/or imperfections of oily skin and/or skin with an oily tendency, and in particular the retentional lesions of open or closed comedone type (microcysts, microcomedones, whiteheads) and/or the imperfections of the type such as dull, glistening or muddy skin, dyschromia, redness, or rough skin, with, as appropriate, patches of dry skin.

According to one particular embodiment, a subject of the invention is the use of the abovementioned microorganism, for the preparation of a composition, in particular a dermatological composition, for treating and/or preventing oily skin or skin with an oily tendency and the associated disorders, such as for example, dermatosis, especially of seborrhoeic type, and in particular acne.

The invention is in particular directed towards the use of such a microorganism for the preparation of a composition, in particular a dermatological composition, for use in the treatment or prevention of acne, and in particular of comedonal, papulopustular and/or nodular acne, acne conglobata and exogenous acne.

Such forms of dermatosis may be the result of a benign condition caused by the excessive proliferation of a fungus and/or of yeast and in particular of yeast of the *Malassezia* genus.

Now, as emerges from the data presented in the examples, the inventors have in particular characterized the ability of a microorganism in accordance with the present invention to stimulate the synthesis of a surprising number of proteins capable of promoting and reinforcing the antimicrobial defences of the epidermis.

In particular, the inventors have demonstrated that a microorganism of the *Lactobacillus paracasei* genus according to the invention makes it possible to stimulate the synthesis of a surprising number of proteins capable of promoting and reinforcing the antimicrobial defences of the epidermis.

In particular, the inventors have demonstrated that such a microorganism makes it possible to stimulate the expression of various antimicrobial defense proteins of the epidermis, such as ribonuclease 7 (Uniref Accession No. Q9H1E1), dermcidin (P81605), "prolactin-inducible protein" (P12273), the S100 A8 and A9 proteins (P05109 and P06702), and the histone protein (Q5R2W0), capable of reinforcing the defences of the epidermis against excessive colonization by pathogenic microorganisms.

Now, this stimulation of the abovementioned proteins has the advantage of effectively opposing a colonization of the epidermis by the microorganisms *Malassezia furfur* and *Propionibacterium acnes*, responsible for the skin disorders associated with oily skin and/or skin with an oily tendency. This decrease obtained by means of said microorganism according to the invention therefore contributes to re-establishing a balanced eco flora with, as a consequence, a decrease in inflammatory conditions of the skin and regulation of seborrhoea. As a result, the imperfections are reduced, the complexion becomes brighter and more homogeneous, without areas of dyschromia, or of dryness.

A treatment in accordance with the invention may prove to be all the more effective on acne and the imperfections of the face if said microorganism combines, with its properties of stimulating the epidermal defense mechanisms, properties of stimulating the synthesis of proteases involved in the desquamation phenomenon KLK7 (Ref. P49862), KLK5 (Q9Y337), cathepsin L2 (O60911)) as attested to by the increase in fragments of corneodesmosome proteins DSG1 (Q02413), DSC1a (Q9HB01), Cdsn (Q15517), induced by the microorganism used according to the present invention. The keratin plug of the comedone can, it appears, then be rapidly eliminated through the action of these proteolytic enzymes, preventing the creation of a closed environment suitable for bacterial development and subsequent inflammation.

The present invention is also directed towards the use of a microorganism in accordance with the invention, for the preparation of a composition, in particular a dermatological composition, for regulating seborrhoea.

The present invention is also directed towards the cosmetic use of an effective amount of at least one probiotic microorganism according to the invention, especially of the *Lactobacillus* and/or *Bifidobacterium* sp. genus and, in particular, of the *Lactobacillus paracasei* ST11 strain, a fraction thereof and/or a metabolite thereof as an active agent for maintaining and/or restoring skin homeostasis.

A use in accordance with the invention may also comprise the use of at least a first probiotic microorganism according to the invention, especially of the *Lactobacillus* and/or *Bifidobacterium* sp. genus and, in particular, of the *Lactobacillus paracasei* ST11 strain, a fraction thereof and/or a metabolite thereof, in combination with an effective amount of at least a second, ancillary microorganism, in particular a probiotic microorganism, distinct from the first microorganism.

A use in accordance with the present invention may also comprise the use of at least one probiotic microorganism according to the invention, especially of the *Lactobacillus* and/or *Bifidobacterium* sp. genus and, in particular, of the *Lactobacillus paracasei* ST11 strain, a fraction thereof and/or a metabolite thereof, in combination with an effective amount of at least one active agent for decreasing and/or correcting excessive sebum secretion, for example an antiseborrhoeic active agent, in particular as described hereinafter.

According to another of its aspects, the present invention relates to a cosmetic composition and/or dermatological composition that is of use for treating and/or preventing oily skin or skin with an oily tendency and the associated aesthetic disorders, comprising, in a physiologically acceptable carrier, at least one probiotic microorganism according to the invention, especially of the *Lactobacillus* and/or *Bifidobacterium* sp. genus, and in particular of the *Lactobacillus paracasei* ST11 strain, a fraction thereof and/or a metabolite thereof in combination with an effective amount of at least one antiseborrhoeic active agent, in particular as described hereinafter.

According to another of its aspects, the subject of the invention is a method, in particular a cosmetic method, for treating and/or preventing oily skin or skin with an oily tendency and the associated disorders, in particular aesthetic disorders, in an individual, comprising at least one step of administering, to said individual, at least one probiotic microorganism according to the invention, especially of the *Lactobacillus* and/or *Bifidobacterium* sp. genus and, in particular, of the *Lactobacillus paracasei* ST11 strain, a fraction thereof and/or a metabolite thereof.

According to one variant embodiment of the invention, a microorganism according to the invention may be used orally.

According to another variant embodiment of the invention, the microorganism according to the invention may be used topically.

However, topical products act, by definition, locally on the areas to be treated, on which areas they may be unequally distributed, and require careful and repeated applications. They may also, in certain cases, be responsible for side reactions on the skin, or even discomfort.

In contrast, oral administration has the advantage of acting globally on the entire skin, in its deep layers (dermis, hypodermis), by means of a rapid and relatively non-restrictive mode of administration. Specifically, the metabolites and other active nutriments are in particular distributed within the dermal matrix by means of the bloodstream.

Oral administration or administration via a patch also has the advantage of a rapid and relatively non-restrictive mode of administration.

According to one preferred embodiment, the cosmetic use according to the invention is therefore carried out orally and the method according to the invention comprises the oral administration of said effective amount of the microorganism under consideration according to the invention, or a fraction thereof.

As specified hereinafter, the compositions containing said microorganism are formulated so as to be compatible with the mode of administration selected.

Microorganisms

A microorganism suitable for the invention is a probiotic microorganism, especially of the *Lactobacillus* and/or *Bifidobacterium* sp. genus.

For the purpose of the present invention, the term "probiotic microorganism" is intended to mean a living microorganism which, when it is consumed in appropriate amount, has a positive effect on the health of its host ("Joint FAO/WHO Expert Consultation on Evaluation of Health and Nutritional Properties of Probiotic in Food Including Powder Milk with Live Lactic Acid Bacteria, 6 Oct. 2001"), and which can in particular improve the intestinal microbial balance.

According to one variant of the invention, this microorganism is used in an isolated form, i.e. not mixed with one or more compound(s) that may be associated with said microorganism in its environment of origin.

For the purpose of the invention, the term "metabolite" denotes any substance derived from the metabolism of the microorganisms under consideration according to the invention and which is also effective in the treatment of oily skin or skin with an oily tendency.

For the purpose of the invention, the term "fraction" denotes more particularly a fragment of said microorganism which is effective in the treatment of oily skin or skin with an oily tendency, by analogy with said whole microorganism.

The microorganisms suitable for the invention may be chosen in particular from ascomycetes such as *Saccharomyces, Yarrowia, Kluyveromyces, Torulaspora, Schizosaccharomyces pombe, Debaromyces, Candida, Pichia, Aspergillus* and *Penicillium*, bacteria of the genus *Bifidobacterium, Bacteroides, Fusobacterium, Melissococcus, Propionibacterium, Enterococcus, Lactococcus, Staphylococcus, Peptostrepococcus, Bacillus, Pediococcus, Micrococcus, Leuconostoc, Weissella, Aerococcus, Oenococcus* and *Lactobacillus*, and mixtures thereof.

As ascomycetes most particularly suitable for the present invention, mention may in particular be made of *Yarrowia lipolitica* and *Kluyveromyces lactis*, and likewise *Saccharomyces cereviseae, Torulaspora, Schizosaccharomyces pombe, Candida* and *Pichia*.

Specific examples of probiotic microorganisms suitable for the invention are *Bifidobacterium adolescentis, Bifidobacterium animalis, Bifidobacterium bifidum, Bifidobacterium breve, Bifidobacterium lactis, Bifidobacterium longum, Bifidobacterium infantis, Bifidobacterium pseudocatenulatum, Lactobacillus acidophilus* (NCFB 1748); *Lactobacillus amylovorus, Lactobacillus casei* (Shirota), *Lactobacillus rhamnosus* (strain GG), *Lactobacillus brevis, Lactobacillus crispatus, Lactobacillus delbrueckii* (subsp *bulgaricus, lactis*), *Lactobacillus fermentum, Lactobacillus helveticus, Lactobacillus gallinarum, Lactobacillus gasseri, Lactobacillus johnsonii* (CNCM I-1225), *Lactobacillus plantarum, Lactobacillus reuteri, Lactobacillus salivarius, Lactobacillus alimentarius, Lactobacillus curvatus, Lactobacillus casei* subsp. *casei, Lactobacillus sake, Lactococcus lactis, Enterococcus (faecalis, faecium), Lactococcus lactis* (subsp *lactis* or *cremoris*), *Leuconostoc mesenteroides* subsp *dextranicum, Pediococcus acidilactici, Sporolactobacillus inulinus, Streptococcus salvarius* subsp. *thermophilus, Streptococcus thermophilus, Staphylococccus carnosus, Staphylococcus xylosus, Saccharomyces(cerevisiae* or else *boulardii), Bacillus (cereus* var toyo or *subtilis), Bacillus coagulans, Bacillus licheniformis, Escherichia coli* strain nissle, *Propionibacterium freudenreichii*, and mixtures thereof.

More particularly, they may be probiotic microorganisms derived from the group of lactic acid bacteria, such as, in particular, *Lactobacillus* and/or *Bifidobacterium*.

By way of illustration of these lactic acid bacteria, mention may more particularly be made of *Lactobacillus johnsonii, Lactobacillus reuteri, Lactobacillus rhamnosus, Lactobacillus paracasei, Lactobacillus casei* or *Bifidobacterium bifidum, Bifidobacterium breve, Bifidobacterium longum, Bifidobacterium animalis, Bifidobacterium lactis, Bifidobacterium infantis, Bifidobacterium adolescentis, Bifidobacterium pseudocatenulatum*, and mixtures thereof.

The species most particularly suitable are *Lactobacillus johnsonii, Lactobacillus paracasei, Bifidobacterium adolescentis* and *Bifidobacterium longum*, respectively deposited according to the Treaty of Budapest with the Institut Pasteur (28 rue du Docteur Roux, F-75024 Paris cedex 15) on 30 Jun. 1992, 12 Jan. 1999, 15 Apr. 1999 and 15 Apr. 1999 under the following designations: CNCM I-1225, CNCM I-2116, CNCM I-2168 and CNCM I-2170, and the *Bifidobacterium lactis* (Bb 12) (ATCC27536) or *Bifidobacterium longum* (BB536) genus. The *Bifidobacterium lactis* (ATCC27536) strain can be obtained from Hansen (Chr. Hansen A/S, 10-12 Boege Alle, P.O. Box 407, DK-2970 Hoersholm, Denmark).

According to one embodiment, a probiotic microorganism suitable for the invention may in particular be a microorganism of the *Lactobacillus* sp. genus.

Preferably, a microorganism of the *Lactobacillus* sp. genus suitable for the invention may be chosen from the species *Lactobacillus johnsonii, Lactobacillus reuteri, Lactobacillus rhamnosus, Lactobacillus paracasei*, and *Lactobacillus casei*, and mixtures thereof.

According to one preferred embodiment, a microorganism suitable for the invention may be a *Lactobacillus paracasei*.

A microorganism suitable for the invention may in particular be the *Lactobacillus paracasei* ST11 strain deposited according to the Treaty of Budapest with the Institut Pasteur (28 rue du Docteur Roux, F-75024 Paris cedex 15) on 12 Jan. 1999 under the designation CNCM I-2116, and/or a fraction thereof and/or a metabolite thereof.

According to one variant embodiment, the invention relates to the use, in addition to a first probiotic microorganism, as defined above, especially of the *Lactobacillus* and/or *Bifidobacterium* sp. genus, of at least an effective amount of at least a second microorganism, in particular of probiotic type, and/or a fraction thereof and/or a metabolite thereof, distinct from said first microorganism.

This second microorganism may be chosen in particular from ascomycetes such as *Saccharomyces, Yarrowia, Kluyveromyces, Torulaspora, Schizosaccharomyces pombe, Debaromyces, Candida, Pichia, Aspergillus* and *Penicillium*, bacteria of the *Bacteroides, Fusobacterium, Melissococcus, Propionibacterium, Enterococcus, Lactococcus, Staphylococcus, Peptostrepococcus, Bacillus, Pediococcus, Micrococcus, Leuconostoc, Weissella, Aerococcus, Oenococcus, Lactobacillus* or *Bifidobacterium* genus, and mixtures thereof.

As ascomycetes most particularly suitable for the present invention, mention may be made in particular of *Yarrowia lipolitica* and *Kluyveromyces lactis*, and likewise *Saccharomyces cereviseae, Torulaspora, Schizosaccharomyces pombe, Candida* and *Pichia*.

Specific examples of probiotic microorganisms are *Lactobacillus acidophilus, Lactobacillus alimentarius, Lactobacillus curvatus, Lactobacillus delbruckii* subsp. *lactis, Lactobacillus gasseri, Lactobacillus johnsonii, Lactobacillus reuteri, Lactobacillus rhamnosus (Lactobacillus GG), Lactobacillus sake, Lactococcus lactis, Streptococcus thermophilus, Staphylococccus carnosus, Staphylococcus xylosus*, and mixtures thereof.

According to one embodiment, the following bacterial and yeast genera are preferentially used as second microorganism:

lactic acid bacteria, which produce lactic acid by fermentation of sugar.

Depending on their morphology, they are divided up into two groups:

*Lactobacillus* species: *Lactobacillus acidophilus, amylovorus, casei, rhamnosus, brevis, crispatus, delbrueckii* (subsp *bulgaricus, lactis*), *fermentum, helveticus, gallinarum, gasseri, johnsonii, plantarum, reuteri, salivarius, alimentarius, curvatus, casei* subsp. *casei, sake*, and

*Gocci*: *Enterococcus (faecalis, faecium), Lactococcus lactis* (subsp *lactis* or *cremoris*), *Leuconostoc mesenteroides* subsp *dextranicum, Pediococcus acidilactici, Sporolactobacillus inulinus, Streptococcus salvarius* subsp. *thermophilus, Streptococcus thermophilus, Staphylococccus carnosus, Staphylococcus xylosus,* bifidobacteria or *Bifidobacterium* species: *Bifidobacterium adolescentis, animalis, bifidum, breve, lactis, longum, infantis, pseudocatenulatum*, yeast: *Saccharomyces (cerevisiae* or else *boulardii*), the other sporulated bacteria: *Bacillus (cereus* var toyo or *subtilis*), *Bacillus coagulans, Bacillus licheniformis, Escherichia coli* strain nissle, *Propionibacterium freudenreichii*, and mixtures thereof.

More particularly, the second microorganism may be one of the probiotic microorganisms proposed above, by way of specific example of probiotic microorganisms for the first microorganism.

The species most particularly suitable are *Lactobacillus johnsonii, Bifidobacterium adolescentis, Bifidobacterium longum* and *Bifidobacterium lactis* NCC 2818, respectively deposited according to the Treaty of Budapest with the Institut Pasteur (28 rue du Docteur Roux, F-75024 Paris cedex 15) on 30 Jun. 1992, 12 Jan. 1999, 15 Apr. 1999, 15 Apr. 1999 and 7 Jun. 2005 under the following designations: CNCM I-1225, CNCM I-2168, CNCM I-2170 and CNCM I-3446, and the *Bifidobacterium longum* (BB536) genus, and mixtures thereof.

According to one particular embodiment, the probiotic microorganism is of the *Lactobacillus species* genus, in particular of the species *Lactobacillus johnsonii*, a fraction thereof and/or a metabolite thereof.

It may in particular be the species *Lactobacillus johnsonii* respectively deposited according to the Treaty of Budapest with the Institut Pasteur (28 rue du Docteur Roux, F-75024 Paris cedex 15) on 30 Jun. 1992, under the designation CNCM I-1225.

A microorganism of the invention may be formulated in a composition in a proportion of at least 0.0001% (expressed by dry weight), in particular in a proportion of from 0.0001% to 20%, and more particularly in a proportion of from 0.001% to 15% by weight, in particular from 0.01% to 10% by weight, and especially from 0.1% to 2% by weight, relative to the total weight of the composition.

In general, a composition according to the invention, and in particular that intended to be administered orally, may comprise, for living microorganisms, from $10^3$ to $10^{15}$ cfu/g, in particular from $10^5$ to $10^{15}$ cfu/g, and more particularly from $10^7$ to $10^{12}$ cfu/g of microorganisms per gram of carrier, or at equivalent doses calculated for inactive or dead microorganisms or for microorganism fractions or for metabolites produced.

In the particular case of the compositions that have to be administered orally, the concentration of each microorganism and/or corresponding fraction and/or metabolite can be adjusted so as to correspond to doses (expressed as microorganism equivalent) ranging from $5 \times 10^5$ to $10^{13}$ cfu/d, and in particular from $10^8$ to $10^{11}$ cfu/d.

A composition for topical application according to the invention may generally comprise from $10^3$ to $10^{12}$ cfu/g, in particular from $10^5$ to $10^{10}$ cfu/g, and more particularly from $10^7$ to $10^9$ cfu/g of microorganisms.

When a composition comprises metabolites, the contents of metabolites in the compositions correspond substantially to the contents capable of being produced by $10^3$ to $10^{15}$ cfu, in particular $10^5$ to $10^{15}$ cfu, and more particularly $10^7$ to $10^{12}$ cfu of living microorganisms per gram of carrier.

The microorganism(s) may be included in a composition according to the invention in a live, semi-active or inactivated, or dead form.

According to one particular embodiment, these microorganisms are used in a live form.

They may also be included in the form of cell component fractions or in the form of metabolites. The microorganism(s), metabolite(s) or fraction(s) may also be introduced in the form of a lyophilized powder, of a culture supernatant and/or where appropriate, in a concentrated form.

According to one variant, the compositions may also contain a divalent inorganic cation.

In the particular case of the topical compositions, it may be advantageous to use these microorganisms in inactivated or even dead form.

The compositions according to the invention may be in any of the galenical forms usually available for the method of administration selected.

Ancillary Active Agent

Irrespective of the method of administration under consideration, the microorganism of the invention may advantageously be combined with at least one other active agent.

Thus, a topical or oral composition according to the invention may also contain at least one antiseborrhoeic active agent.

Such a formulation may advantageously amplify the beneficial effects of a microorganism of the invention.

The term "antiseborrhoeic active agent" is intended to mean a compound capable of regulating sebaceous gland activity.

An antiseborrhoeic active agent suitable for the invention may in particular be chosen from retinoic acid, benzoyl peroxide, sulphur, vitamin B6 (or pyridoxine), selenium chloride, sea fennel; mixtures of extract of cinnamon, of tea and of octanoylglycine, such as SEPICONTROL A5 TEA® from Seppic; the mixture of cinnamon, sarcosine and octanoylglycine sold in particular by the company SEPPIC under the trade name SEPICONTROL A5®; zinc salts such as zinc gluconate, zinc pyrrolidonecarboxylate (or zinc pidolate), zinc lactate, zinc aspartate, zinc carboxylate, zinc salicylate, zinc cysteate; copper derivatives, and in particular copper pidolate such as CUIVRIDONE® from Solabia; extracts of plants of the species *Arnica montana, Cinchona succirubra, Eugenia caryophyllata, Humulus lupulus, Hypericum perforatum, Mentha piperita, Rosmarinus officinalis, Salvia officinalis* and *Thymus vulgaris*, all sold, for example, by the company Maruzen; extracts of meadowsweet (*Spiraea* ulmaria) such as the product sold under the name SEBONORMINE® by the company Silab; extracts of the alga *Laminaria saccharina* such as the product sold under the name PHLOROGINE® by the company Biotechmarine; mixtures of extracts of salad burnet root (Sanguisorba officinalis/Poterium officinale), of ginger rhizomes (*Zingiber officinalis*) and of cinnamon bark (*Cinnamomum cassia*), such as the product sold under the name SEBUSTOP® by the company Solabia; linseed extracts, such as the product sold under the name Linumine® by the company Lucas Meyer; Phellodendron extracts, such as those sold under the name PHELLODENDRON EXTRACT BG® by the company Maruzen or Oubaku liquid B by the company Ichimaru Pharcos; mixtures of argan oil, of *Serenoa serrulata* (saw palmetto) extract and of sesame seed extract, such as the product sold under the name REGU SEB® by the company Pentapharm; mixtures of extracts of willowherb, of Terminalia chebula, of nasturtium and of bioavailable zinc (microalgae), such as the product sold under the name SEBORILYS® by the company Green Tech; extracts of Pygeum afrianum, such as the product sold under the name Pygeum afrianum sterolic lipid Extract® by the company Euromed; extracts of *Serenoa serrulata*, such as those sold under the name VIAPURE SABAL® by the company Actives International, or those sold by the company Euromed; mixtures of extracts of plantain, of *Berberis aquifolium* and of sodium salicylate, such as the product sold under the name SEBOCLEAR® by the company Rahn; clove extract, such as the product sold under the name Clove extract Powder® by the company Maruzen; argan oil, such as the product sold under the name LIPOFRUCTYL® by Laboratoires Serobiologiques; lactic protein filtrates, such as the product sold under the name NOMASEB® by the company Sederma; extracts of the alga *Laminaria*, such as the product sold under the name LAMINARGHANE® by the company Biotechmarine; oligosaccharides of the alga *Laminaria digitata*, such as the product sold under the name PHYCOSACCHARIDEAC® by the company Codif; cane sugar extracts, such as the product sold under the name POLICOSANOL® by the company Sabinsa; sulphonated shale oil, such as the product sold under the name ICHTHYOL PALE® by the company Ichthyol; extracts of European meadowsweet (*Spiraea ulmaria*), such as the product sold under the name CYTOBIOL® Ulmaire by the company Libiol; sebacic acid, in particular sold in the form of a sodium polyacrylate gel under the name SEBOSOFT® by the company Sederma; glucomannans extracted from konjac tuber and modified with alkylsulphonate chains, such as the product sold under the name BIOPOL BETA® by the company Arch Chemical;

extracts of *Sophora angustifolia*, such as those sold under the name SOPHORA POWDER® or SOPHORA EXTRACT® by the company Bio land; extracts of *Cinchona succirubra* bark, such as the product sold under the name RED BARK HS® by the company Alban Muller; extracts of *Quillaja saponaria*, such as the product sold under the name PANAMA WOOD HS® by the company Alban Muller; glycine grafted onto an undecylenic chain, such as the product sold under the name LIPACIDE UG OR® by the company Seppic; the mixture of oleanolic acid and of nordihydroguaiaretic acid, such as the product sold in the form of a gel under the name AC.Net® by the company Sederma; phthalimidoperoxyhexanoic acid; tri(Ci2-Ci3)alkyl citrate sold under the name COSMACOL® ECI by the company Sasol; tri(Ci4-Ci5)alkyl citrate sold under the name COMACOL® ECL by the company Sasol; 10-hydroxydecanoic acid, and in particular mixtures of 10-hydroxydecanoic acid, of sebacic acid and of 1,10-decanediol, such as the product sold under the name ACNACIDOL® BG by the company Vincience; and mixtures thereof.

The antiseborrhoeic active agent is, for example, present in a content ranging from 0.1% to 10% by weight, preferably from 0.1% to 5% by weight, and preferentially from 0.5% to 3% by weight, relative to the total weight of the composition.

In addition to this antiseborrhoeic active agent, the compositions according to the invention may also contain several other active agents commonly used and/or permitted.

As active agents that are conventionally used, mention may be made of vitamins B3, B5, B6, B8, C, D, E, or PP, niacin, carotenoids, polyphenols, minerals and trace elements, phytoestrogens, proteins and amino acids, monosaccharides and polysaccharides, amino sugars, phytosterols and triterpenic alcohols of plant origin.

The minerals and trace elements particularly used are zinc, calcium, magnesium, copper, iron, iodine, manganese, selenium, and chromium(III).

Among the polyphenols, polyphenols from grape, from tea, from olive, from cocoa, from coffee, from apple, from blueberry, from elderberry, from strawberry, from cranberry and from onion are also in particular selected. Preferably, among the phytoestrogens, isoflavones in free or glycosylated form are selected, such as genistein, daidzein, glycitein or else lignans, in particular those from flax and from *Schizandra chinensis*.

The amino acids or the peptides and the proteins containing them, such as taurine, threonine, cysteine, tryptophan, or methionine. The lipids preferably belong to the group of oils containing monounsaturated and polyunsaturated fatty acids such as oleic acid, linoleic acid, alpha-linolenic acid, gamma-linolenic acid, stearidonic acid, long-chain fish omega-3 fatty acids, such as EPA and DHA, or conjugated fatty acids derived from plants or from animals, such as CLAs (conjugated linoleic acids).

In particular, use may be made of an antioxidant complex comprising vitamins C and E, and at least one carotenoid, in particular a carotenoid chosen from β-carotene, lycopene, astaxanthin, zeaxanthin and lutein, flavonoids, such as catechins, hesperidin, proanthocyanidins and anthocyanins, lipoic acid and coenzyme Q10.

The ancillary active agent may also be at least one prebiotic or a mixture of prebiotics. More particularly, these prebiotics may be chosen from oligosaccharides, produced from glucose, galactose, xylose, maltose, sucrose, lactose, starch, xylan, hemicellulose or inulin, gums of acacia type for example, or a mixture thereof.

More particularly, the oligosaccharide comprises at least one fructooligosaccharide. More particularly, this prebiotic may comprise a mixture of fructo-oligosaccharide and inulin.

In the topical galenical forms, use may more particularly be made, as hydrophilic active agents, of proteins or protein hydrolyzates, amino acids, polyols, in particular $C_2$ to $C_{10}$ polyols such as glycerol, sorbitol, butylene glycol and polyethylene glycol, urea, allantoin, sugars and sugar derivatives, water-soluble vitamins, starch, bacterial extracts or plant extracts such as those of *Aloe Vera*.

As regards the lipophilic active agents, use may be made of retinol (vitamin A) and its derivatives, tocopherol (vitamin E) and its derivatives, ceramides, essential oils and unsaponifiable materials (tocotrienol, sesamine, gamma-oryzanol, phytosterols, squalenes, waxes and terpenes).

It is possible to advantageously combine, with the product, active agents for promoting desquamation, such as the reference hydrating active agents in cosmetics: glycerol, hyaluronic acid, urea and its derivatives, and also active agents for promoting desquamation and peeling, such as chelating agents, jasmonic acid and its derivatives, in particular ER2412, reducing compounds, sulfonic derivatives and in particular Hepes, amino acids, AHA and BHA, most particularly glycolic acid and ER195, and certain detergents.

Galenical Forms

The compositions according to the invention may be in any of the galenical forms normally available for the method of administration selected.

The carrier may be of diverse nature depending on the type of composition under consideration. The compositions for topical administration may be aqueous, aqueous-alcoholic or oily solutions, dispersions of the solution type or dispersions of the lotion or serum type, emulsions of liquid or semi-liquid consistency, of the milk type, suspensions or emulsions of the cream type, aqueous or anhydrous gels, microemulsions, microcapsules, microparticles, or vesicular dispersions of ionic and/or nonionic type.

These compositions are prepared according to the usual methods.

These compositions may constitute in particular cleansing, peeling, treatment or care creams for the face, for the hands, for the feet, for the major anatomical folds or for the body (for example, day creams, night creams, makeup removing creams, foundation creams, antisun creams), makeup products such as fluid foundations, makeup-removing milks, protective or care body milks, aftersun milks, skincare lotions, gels or mousses, such as cleansing or disinfecting lotions, antisun lotions, artificial tanning lotions, or bath compositions.

The compositions according to the invention may also consist of solid preparations constituting cleansing soaps or bars.

When the composition of the invention is an emulsion, the proportion of the fatty phase may range from 5% to 80% by weight, and preferably from 5% to 50% by weight, relative to the total weight of the composition. The oils, the emulsifiers and the coemulsifiers used in the composition in emulsion form are chosen from those conventionally used in the cosmetics and/or dermatological field. The emulsifier and the coemulsifier may be present, in the composition, in a proportion ranging from 0.3% to 30% by weight, and preferably from 0.5% to 20% by weight, relative to the total weight of the composition.

When the composition of the invention is an oily gel or solution, the fatty phase may represent more than 90% of the total weight of the composition.

In a known manner, the galenical forms for topical administration may also contain adjuvants that are customary in the cosmetics, pharmaceutical and/or dermatological field, such as hydrophilic or lipophilic gelling agents, hydrophilic or lipophilic active agents, preservatives, antioxidants, solvents, fragrances, fillers, screens, bactericides, odour absorbers and dyestuffs. The amounts of these various adjuvants are those conventionally used in the field under consideration, and are, for example, from 0.01% to 20% of the total weight of the composition. Depending on their nature, these adjuvants may be introduced into the fatty phase and/or into the aqueous phase.

As fats that can be used in the invention, mention may be made of mineral oils such as, for example, hydrogenated polyisobutene and liquid petroleum jelly, plant oils such as, for example, a liquid fraction of shea butter, sunflower oil and apricot kernel oil, animal oils such as, for example, perhydrosqualene, synthetic oils, in particular Purcellin oil, isopropyl myristate and ethylhexyl palmitate, unsaturated fatty acids and fluoro oils such as, for example, perfluoropolyethers. Use may also be made of fatty alcohols, fatty acids such as, for example, stearic acid and such as, for example, waxes, in particular paraffin wax, carnauba wax and beeswax.

Use may also be made of silicone compounds such as silicone oils and, for example, cyclomethicone and dimethicone, and silicone waxes, resins and gums.

As emulsifiers that can be used in the invention, mention may, for example, be made of glyceryl stearate, polysorbate 60, the mixture of cetylstearyl alcohol/oxyethylenated cetylstearyl alcohol comprising 33 mol of ethylene oxide, sold under the name Sinnowax AO® by the company Henkel, the mixture of PEG-6/PEG-32/glycol stearate sold under the name Tefose® 63 by the company Gattefosse, PPG-3 myristyl ether, silicone emulsifiers such as cetyl dimethicone copolyol and sorbitan monostearate or tristearate, PEG-40 stearate, or oxyethylenated sorbitan monostearate (20 EO).

As solvents that can be used in the invention, mention may be made of lower alcohols, in particular ethanol and isopropanol, and propylene glycol.

A composition of the invention may also advantageously contain a spring and/or mineral water, in particular chosen from Vittel water, waters from the Vichy basin, and la Roche Posay water.

As hydrophilic gelling agents, mention may be made of carboxylic polymers such as carbomer, acrylic copolymers such as acrylate/alkyl acrylate copolymers, polyacrylamides, and in particular the mixture of polyacrylamide, C13-14 isoparaffin and Laureth-7 sold under the name Sepigel 305® by the company SEPPIC, polysaccharides, for instance cellulosic derivatives such as hydroxyalkylcelluloses, and in particular hydroxypropylcellulose and hydroxyethylcellulose, natural gums such as guar, carob and xanthan, and clays.

As lipophilic gelling agents, mention may be made of modified clays such as bentones, metal salts of fatty acids, such as aluminium stearates and hydrophobic silica, or else ethylcellulose and polyethylene.

In the case of a use in accordance with the invention by oral administration, use of an ingestible carrier is preferred.

The ingestible carrier may be of diverse nature depending on the type of composition under consideration.

Tablets or lozenges, oral supplements in dry form and oral supplements in liquid form are thus in particular suitable for use as pharmaceutical or food carriers.

They may, for example, be food supplements, the formulation of which may be performed via the usual processes for in particular producing sugar-coated tablets, gel capsules, gels, emulsions, tablets, capsules and hydrogels allowing controlled release.

In particular, the microorganism according to the invention may be incorporated into any other form of food supplement or enriched food, for example food bars or compacted or non-compacted powders. The powders may be diluted in water, soda, milk products or soya bean derivatives, or be incorporated into food bars.

The microorganism, according to the invention, may, moreover, be formulated with the excipients and components that are customary for such oral compositions or food supplements, i.e. in particular, fatty and/or aqueous components, humectants, thickeners, preservatives, texturing agents, flavour enhancers and/or coating agents, antioxidants, preservatives and dyes that are customary in the food sector.

The formulating agents and excipients for oral compositions, and in particular for food supplements, are known in this field and will not be the subject of a detailed description herein.

Milk, yogurt, cheese, fermented milks, milk-based fermented products, ices, cereal-based products or fermented cereal-based products, milk-based powders, infant and baby formulas, food products of confectionery, chocolate or cereal type, animal feed, in particular for domestic animals, tablets, gel capsules or lozenges, liquid bacterial suspensions, oral supplements in dry form and oral supplements in liquid form are especially suitable as pharmaceutical or food carriers.

A microorganism in accordance with the invention may, moreover, be formulated with the excipients and components that are customary for such oral compositions or food supplements, i.e. in particular, fatty and/or aqueous components, humectants, thickeners, preservatives, texturing agents, flavour enhancers and/or coating agents, antioxidants, preservatives and dyes that are customary in the food sector.

The formulating agents and excipients for oral compositions, and in particular for food supplements, are known in this field and will not be the subject of a detailed description herein. Many embodiments of oral compositions and in particular of food supplements are possible for ingestion. The formulation thereof is carried out by means of the usual methods for producing sugar-coated tablets, gel capsules, gels, hydrogels for controlled release, emulsions, tablets or capsules.

According to one particular embodiment, the ancillary microorganisms under consideration according to the invention may be formulated in compositions in an encapsulated form so as to significantly improve their survival time. In such a case, the presence of a capsule in particular may delay or prevent the degradation of the microorganism in the gastrointestinal tract.

The cosmetic treatment method of the invention may be carried out in particular by orally and/or topically administering at least an effective amount of at least one microorganism in accordance with the invention.

Topical administration comprises the external application, to the skin, of cosmetic and/or dermatological compositions according to the customary technique for using these compositions.

By way of illustration, the cosmetic method according to the invention may be carried out by topical application, for example daily, of the microorganism in accordance with the invention, which may, for example, be formulated in the form of creams, gels, sera, lotions, emulsions, milks for removing makeup or aftersun compositions.

The method according to the invention may comprise a single application. According to another embodiment, the application is repeated, for example, 2 to 3 times a day, for one day or more, and generally for a sustained period of at least 4, or even 1 to 15, weeks.

Oral administration comprises ingesting, in one or more intakes, an oral composition as defined above.

In the description and in the examples which follow, unless otherwise indicated, the percentages are percentages by weight and the ranges of values written in the form "between . . . and . . . " include the upper and lower limits specified. The ingredients are mixed, before they are formulated, in the order and under conditions readily determined by those skilled in the art.

According to one variant, the cosmetic method comprises at least one step of orally administering an effective amount of at least one microorganism according to the invention, or of a fraction thereof, and at least one step of topically administering an effective amount of at least one microorganism according to the invention or of a fraction thereof.

The method according to the invention may comprise a single administration.

According to another embodiment, the administration is repeated, for example, 2 to 3 times a day, for one day or more and generally for a sustained period of at least 4 weeks, or even 4 to 15 weeks, with, where appropriate, one or more periods of interruption.

In addition, combinations of treatment with, optionally, oral or topical forms may be envisaged in order to supplement or reinforce the activity of the microorganism as defined by the invention.

Thus, a topical treatment with a composition containing a microorganism in accordance with the invention, combined with an oral or topical composition optionally containing another microorganism, in particular a probiotic microorganism, or other probiotics in dead, live or semi-active form could be imagined.

The ingredients are mixed, before they are formulated, in the order and under conditions readily determined by those skilled in the art.

The examples hereinafter are presented by way of nonlimiting illustration of the field of the invention.

In these examples, the term "cfu" denotes "colony forming unit". This is the unit of measurement used to quantify live bacteria.

The *Lactobacillus paracasei* used in the compositions of the examples hereinafter is *Lactobacillus paracasei* ST11 NCC 2461 (CNCM I-2116).

EXAMPLES OF COMPOSITIONS FOR ORAL ADMINISTRATION

Example 1

Powder Stick

| Ingredients | Amount |
| --- | --- |
| Active ingredient | |
| *Lactobacillus paracasei* ST11 | $10^{10}$ cfu |
| Excipient | |
| Maltodextrin | qs 30 g |
| Xanthan gum | 0.8 mg |
| Sodium benzoate | 0.2 mg |

One stick can be taken per day.

Example 2

Capsule

| Ingredients | Amount mg/capsule |
| --- | --- |
| *Lactobacillus paracasei* ST11 | $10^9$ cfu |
| *Lactobacillus johnsonii* | $10^8$ cfu |
| Vitamin C | 60 |
| Magnesium stearate | 0.02 |

One to three of these capsules can be taken per day.

Example 3

Formulation of Sugar-Coated Tablet Type

| Ingredients | Mg/sugar-coated tablet |
| --- | --- |
| Active ingredient | |
| *Lactobacillus paracasei* ST11 | $5 \times 10^8$ cfu |
| Excipient of the sugar-coated tablet core | |
| Microcrystalline cellulose | 70 |
| Encompress ® | 60 |
| Magnesium stearate | 3 |
| Anhydrous colloidal silica | 1 |
| Coating agent | |
| Shellac | 5 |
| Talc | 61 |
| Sucrose | 250 |
| Polyvidone | 6 |
| Titanium dioxide | 0.3 |
| Colouring agent | 5 |

This type of sugar-coated tablet can be taken 1 to 3 times per day.

Example 4

Formulation of Sugar-Coated Tablet Type

| Ingredients | Mg/sugar-coated tablet |
| --- | --- |
| Active ingredient | |
| *Lactobacillus paracasei* ST11 | $10^9$ cfu |
| *Lactobacillus johnsonii* | $10^9$ cfu |
| Excipient of the sugar-coated tablet core | |
| Microcrystalline cellulose | 70 |
| Encompress ® | 60 |
| Magnesium stearate | 3 |
| Anhydrous colloidal silica | 1 |
| Coating agent | |
| Shellac | 5 |
| Talc | 61 |
| Sucrose | 250 |
| Polyvidone | 6 |
| Titanium dioxide | 0.3 |
| Colouring agent | 5 |

This type of sugar-coated tablet can be taken 1 to 3 times per day.

Examples of Compositions For Topical Application

Example 5

Face Lotion

| Ingredients | Amount (%) |
| --- | --- |
| *Lactobacillus paracasei* ST11 powder | 5.00 |
| *Lactobacillus johnsonii* powder | 5.00 |
| Anti-inflammatory | 0.05 |
| Antioxidant | 0.05 |
| Isopropanol | 40.00 |
| Preservative | 0.30 |
| Water | Qs 100 |

Example 6

Scalp Care Milk

| Ingredients | Amount (%) |
| --- | --- |
| *Lactobacillus paracasei* ST11 powder | 5.00 |
| Glyceryl stearate | 1.00 |
| Cetylstearyl alcohol/oxyethylenated cetylstearyl alcohol comprising 30 mol EO (Sinnowax AO ® sold by the company Henkel) | 3.00 |
| Cetyl alcohol | 1.00 |
| Dimethicone (DC 200 Fluid ® sold by the company Dow Corning) | 1.00 |
| Liquid petroleum jelly | 6.00 |
| Isopropyl myristate (Estol IPM 1514 sold by Unichema) | 3.00 |
| Antioxidant | 0.05 |
| Glycerol | 20.00 |
| Isopropanol | 40.00 |
| Preservative | 0.30 |
| Water | Qs 100 |

Example 7

Face Care Gel

| Ingredients | Amount (%) |
| --- | --- |
| *Lactobacillus paracasei* ST11 powder | 5.00 |
| Hydroxypropylcellulose (Klucel H ® sold by the company Hercules) | 5.00 |
| Vitamin E | 2.50 |
| Antioxidant | 0.05 |
| Isopropanol | 40.00 |
| Preservative | 0.30 |
| Water | Qs 100 |

Example 8

Scalp Care Milk

| Ingredients | Amount (%) |
| --- | --- |
| *Lactobacillus paracasei* ST11 powder | 5.00 |
| Glyceryl stearate | 1.00 |
| Cetylstearyl alcohol/oxyethylenated cetylstearyl alcohol comprising 3 mol EO (Sinnowax AO ® sold by the company Henkel) | 3.00 |
| Cetyl alcohol | 1.00 |
| Dimethicone (DC 200 Fluid ® sold by the company Dow Corning) | 1.00 |
| Liquid petroleum jelly | 6.00 |
| Isopropyl myristate (Estol IPM 1514 sold by Unichema) | 3.00 |
| Glycerol | 20.00 |
| Preservative | 0.30 |
| Water | Qs 100 |

Example 9

Face Care Cream

| Ingredients | Amount (%) |
| --- | --- |
| Arachidyl behenyl alcohol/arachidylglucoside | 3.00 |
| Isohexadecane | 7.00 |
| *Lactobacillus paracasei* ST11 powder | 5.00 |
| Glycerol | 2.00 |
| Extract of *Vitreoscilla filiformis* | 3.00 |
| BHT | 0.05 |
| Methyl POB | 0.10 |
| Propyl POB | 0.05 |
| Water | qs 100 |

Example 10

Face Care Gel

| Ingredients | Amount (%) |
| --- | --- |
| *Lactobacillus paracasei* ST11 powder | 5.00 |
| Extract of *Vitreoscilla filiformis* | 5.00 |
| Antioxidant | 0.05 |
| Vitamin C | 2.50 |
| Isopropanol | 40.00 |
| Preservative | 0.30 |
| Water | qs 100 |

Example 11

Effect of a Food Supplement Comprising a Microorganism in Accordance With the Invention on Acne and Facial Imperfections in Adult Women The *Lactobacillus paracasei* ST11 NCC 2461 (CNCM I-2116) strain was tested alone, in a randomized double-blind study.

Women between 18 and 40 years of age, having acneic skin and facial imperfections, were divided up into several groups:

a first group of 33 women, to which a placebo was administered, the placebo being an identical composition, but containing maltodextrin in place of the microorganism (hereinafter referred to as "product A"), and a second group of 33 women, to which a composition containing $1 \times 10^9$ cfu of the abovementioned *Lactobacillus paracasei* ST11, alone, (hereinafter referred to as "product B") was administered.

These food supplements were administered orally, for 2 months.

The individuals were evaluated at D1, D15, D29, D43 and D57 by means of various clinical evaluations.

In particular, a clinical evaluation of the facial imperfections such as dyschromia was carried out and the individuals themselves carried out a self-evaluation of the improvement in the condition of their skin.

a) Clinical Evaluations

The principle criterion for judging effectiveness is defined by the number of superficial inflammatory lesions (papules and pustules, without distinction) and the number of retentional lesions (open and closed comedones, without distinction).

The counts are performed by the investigator at each consultation (D1, D15, D29, D43 and D57) over the entire face (including the chin, but not on the T zone) by visual counting, according to the ECLA scale:

Factor F 1: Type and Intensity of the Acne on the Entire Face With Scores of 0 to 5 (Corresponding to a Lesion Count (0; <5; 5 to 9; 10 to 19; 20 to 40; >40)

Non-inflamed lesions: Open and closed comedones with scores of 0 to 5 (corresponding to a lesion count) (0; <5; 5 to 9; 10 to 19; 20 to 40; >40).

Inflamed lesions:
- a) Superficial: papules and pustules with scores of 0 to 5 (corresponding to a lesion count (0; <5; 5 to 9; 10 to 19; 20 to 40; >40), and information on the size (from 0.1 cm to 0.5 cm)
- b) Deep: nodules and cysts with scores of 0 to 5 (corresponding to a lesion count (0, 1, 2, 3, 4, 5), and information on the size (0.5 cm or more).

Factor F 2: Extension and Intensity of the Acne Beyond the Face

Neck with grading from 0 (absent) to 3 (considerable) of the top and bottom cervical zone,
Chest with grading from 0 (absent) to 3 (considerable),
Back with grading from 0 (absent) to 3 (considerable) (upper scapula tip and lower scapula tip),
Arm with grading from 0 (absent) to 3 (considerable).

Factor F 3: Scars
Absent (0) or present (1).
They may be inflammatory, noninflammatory or excoriated.

Furthermore, the investigator evaluates, at each consultation (D1, D15, D29, D43 and D57), on scales of 0 to 9:
the presence of marks (freckles, actinic marks, depigmentation, beauty spots),
withering,
the presence of dry patches,
scales,
seborrhoeic dermatitis.

The result of this evaluation is that the food supplement tested makes it possible to significantly reduce the number of superficial inflammatory lesions and the number of retentional lesions, compared with the placebo composition.

b) Evaluation of Seborrhoea

The amount of sebum excreted at the surface of the skin is evaluated using a Sebumetre® (Courage & Khazaka).

It is a photometric method. A strip of synthetic material, which becomes transparent in contact with absorbed lipids, is applied to the measurement zone for precisely 30 seconds.

The transparency of said strip then increases proportionally to the amount of sebum of the hydrolipid film with which it is in contact.

Recording by reflectometry makes it possible to quantify the increase in transmitted light and thus to determine the total mass of lipids excreted per unit surface area (in $\mu g \cdot cm^{-2}$).

A measurement is carried out on the forehead after careful delipidation with 70° alcohol.

Then, after half an hour, a further measurement is carried out. It is thus possible to calculate the amount of sebum excreted per unit of surface area and per unit of time.

The result of this test is that the food supplement tested makes it possible to reduce re-oiling of the skin by 50%, compared with the placebo composition.

c) Analysis of the General Ecoflora of the Face

At each visit, bacteriological samples are taken, on the face of the individuals, with 2 sterile SWABs (Oxoid) for the bacterial ecoflora.

Methodology:

2 zones of approximately 5 cm by 1 cm are delimited on each side of the nose (1 on the left and 1 on the right).

The locations selected are indicated in the observation notebook and will remain the same for a given individual throughout the study (and are pinpointed on the basis of measurements from the tip of the nose and the top of the ears).

With each of the 2 swabs, the face is rubbed 5 times and then, after having turned the swab around, it is rubbed again twice.

The swab is closed and stored at +4° C. before transfer to the bacteriology department.

The two swabs are combined in 3 ml of PBS containing 0.1% of Triton X, and vigorously agitated for at least 30 seconds.

This suspension represents the stock solution (SS) from which two successive ten-fold dilutions ($1/10^{th}$—d1 and d2) will be carried out.

0.1 ml of SS will be plated out at the surface of the agar in order to search for *Escherichia coli* and *Staphylococcus aureus*.

0.1 ml of SS, 0.1 ml of d1 and 0.1 ml of d2 will be plated out at the surface of the agar for the total flora, the anaerobic flora, the gram+cocci and the corynebacteria.

All the inoculations will be performed in duplicate.

*Escherichia coli, Staphylococcus aureus*, the total flora, the gram+cocci and the corynebacteria are incubated at 35-37° C. under aerobic conditions for 48 h.

The anaerobic flora is incubated at 35-37° C. under anaerobic conditions for 5 to 6 days.

A blood medium is used (8 days at 37° C. under anaerobic conditions) for counting *Propionibacterium*, essentially *P. acnes*, for the skin flora.

| Summarizing table | | | |
|---|---|---|---|
| Ecoflora | Dilutions | Media | Description |
| Total flora | SS, d1, d2 | TS* + 1% Tween 80 Aerobic conditions 37° C. - 48 H | Non-selective base medium |
| Gram "+" cocci | SS, d1, d2 | Columbia ANC** + 5% sheep blood Aerobic conditions 37° C. - 48 H | Medium selective for gram "+" cocci by addition of the ANC antibiotic mixture (nalidixic acid and colistin) inhibiting growth of gram "−" bacilli |
| Anaerobic flora *P acnes* | SS, d1, d2 | Columbia + 5% sheep blood Anaerobic conditions 37° C. - 5 days | Incubation in the absence of oxygen |

Summarizing table

| Ecoflora | Dilutions | Media | Description |
|---|---|---|---|
| Corynebacteria | SS, d1, d2 | Columbia + 5% sheep blood<br>Aerobic conditions<br>37° C. - 48 H | |
| *Escherichia coli* | SS | Drigalski medium<br>Aerobic conditions<br>37° C. - 48 H | Medium selective for *enterobacteria* by addition of crystal violet which inhibits gram+ bacteria. Reveals lactose "+" bacteria. |
| Coagulase "+" staphylococci | SS | Baird Parker + RPF<br>Aerobic conditions<br>37° C. - 48 H | Medium selective for coagulase "+" staphylococci with direct reading of staphylocoagulase. |

The counting indicates that the anaerobic flora (and in particular *Propionibacterium acnes* and corynebacteria) is reduced in patients having followed the treatment with the food supplement containing the active agent under consideration, thus contributing to the reestablishment of homeostasis of the skin.

d) Protein Expression

In addition, at times D1, D29 and D57 samples were taken from the forehead, with corneodiscs in order to study the epidermal protein expression of treated individuals.

Corneodiscs are adhesive discs made of a flexible, transparent polyester film coated with an adhesive, which is itself transparent, that are relatively insensitive to oxidation and to dust and provide good contact with the stratum corneum. This technique makes it possible to analyse the composition of certain proteins of the horny layer.

Application using a calibrated dynamometer is recommended in order to obtain a constant application pressure of between 100 and 250 g/cm$^2$. A clean and dry surface allows optimal adhesion in the space of 5 seconds.

Methodology:

A rectangle of 1×2 cm is delimited on a zone of the forehead.

The corneodisc is placed on the mini-zone. The corneodisc is then folded in half, back on itself, with adhesion of the white border and placed in a Nunc tube.

3 corneodiscs are thus recovered successively from the same zone, and the three Nunc tubes are then introduced into liquid nitrogen and stored at −80° C. before the quantitative analysis of defensins (more particularly beta-defensin type 2, LL-37, elafin) and of the inflammatory markers (TNF-alpha, IL-6, IL-8).

Sampling is carried out on the forehead at times D1, D29, and D57 by corneodisc, so as to sample only a part of the stratum corneum, i.e. a maximum of 4 to 5 layers of stratum corneum.

These skin samples were subsequently analysed, after extraction, by ELISA analysis and by the luminex technique.

These analyses made it possible to show that the microorganism in accordance with the invention stimulates the expression of some of the antimicrobial defense proteins of the epidermis (LL37, beta-defensin 2 and elafin) and certain proinflammatory cytokines (TNF-alpha and IL8).

The demonstration of the abovementioned proteins is thus linked to decreased colonization by the *Malassezia furfur* and *Propionibacterium acnes* microorganisms responsible for the skin disorders associated with oily skin and/or skin with an oily tendency.

In addition, reducing inflammatory cytokines also participates in the reduction of skin disorders associated with oily skin and/or skin with an oily tendency.

Thus, such a reduction contributes to re-establishing a balanced ecoflora, the consequence of which is a decrease in inflammatory conditions of the skin and regulation of seborrhoea. Consequently, the imperfections are reduced, and the complexion becomes brighter and more homogeneous, without areas of dyschromia and of dryness.

These results show a positive effect for treating and/or preventing oily skin or skin with an oily tendency and the associated skin disorders, and allowing a reduction in the associated skin disorders, such as retentional lesions of open or closed comedone type (microcyst, microcomedone, whiteheads) and/or skin imperfections of dull, glistening or muddy skin, or dyschromia type.

The invention claimed is:

1. A method of treating oily skin or skin with an oily tendency and an associated skin disorder, the method comprising orally administering a cosmetic composition comprising an effective amount of a single probiotic microorganism *Lactobacillus paracasei*, to a subject in need thereof, wherein the composition does not include a divalent inorganic cation.

2. The method of claim 1, comprising treating an associated skin disorder and wherein the associated skin disorder is a retentional lesion of open or closed comedone type or a skin imperfection selected from the group consisting of dull skin, glistening skin, muddy skin, dyschromia, redness, and rough skin.

3. The method of claim 1, comprising treating an associated skin disorder and wherein the associated skin disorder is a seborrhoeic dermatosis.

4. The method of claim 1, comprising treating an associated skin disorder and wherein the associated skin disorder is acne.

5. The method of claim 1, comprising treating an associated skin disorder and wherein the associated skin disorder is seborrhoea.

6. The method of claim 4, wherein the acne is comedonal acne, papulopustular acne, nodular acne, acne conglobata or exogenous acne.

7. The method of claim 1, wherein the probiotic microorganism is *Lactobacillus paracasei* CNCM 1-2116.

8. The method of claim 1, wherein the probiotic microorganism is present in an amount of from 0.0001% to 20% by weight relative to the total weight of the cosmetic composition.

9. The method of claim 8, wherein the probiotic microorganism is administered present in an amount of from 0.001% to 15% by weight relative to the total weight of the cosmetic composition.

10. The method of claim 8, wherein the probiotic microorganism is administered present in an amount of from 0.01% to 10% by weight relative to the total weight of the cosmetic composition.

* * * * *

UNITED STATES PATENT AND TRADEMARK OFFICE
CERTIFICATE OF CORRECTION

| | | |
|---|---|---|
| PATENT NO. | : 8,951,775 B2 | Page 1 of 1 |
| APPLICATION NO. | : 13/056344 | |
| DATED | : February 10, 2015 | |
| INVENTOR(S) | : Isabelle Castiel et al. | |

It is certified that error appears in the above-identified patent and that said Letters Patent is hereby corrected as shown below:

Title Page, insert --Related U.S. Application Data

(60) Provisional Application 61/084,580, filed July 29, 2008--.

Signed and Sealed this
Third Day of November, 2015

Michelle K. Lee
*Director of the United States Patent and Trademark Office*